US00PP08475P

United States Patent [19]

Riordan et al.

[11] Patent Number: Plant 8,475

[45] Date of Patent: Nov. 23, 1993

[54] 609 BUFFALOGRASS

[75] Inventors: Terrance P. Riordan; Frederick P. Baxendale; Susan A. de Shazer; Edward J. Kinbacher, all of Lincoln, Nebr.; Jeana L. F. Svoboda, Altus, Okla.; Milton C. Engelke, Richardson, Tex.; Leonard A. Wit, Jr., Bennet, Nebr.

[73] Assignee: The Board of Regents of the University of Nebraska, Lincoln, Nebr.

[21] Appl. No.: 755,829

[22] Filed: Sep. 6, 1991

[51] Int. Cl.[5] ..... A01H 5/00

[52] U.S. Cl. ..... Plt./90

[58] Field of Search ..... Plt./90

[56] References Cited

U.S. PATENT DOCUMENTS

P.P. 7,539 5/1991 Engelke et al. ..... Plt. 90

*Primary Examiner*—James R. Feyrer

*Attorney, Agent, or Firm*—Vincent L. Carney

[57] ABSTRACT

A vegetatively reproduced buffalograss cultivar, named 609 Buffalograss, is distinguished by its excellent overall turfgrass quality, rate of establishment, good cold tolerance, high density, and excellent color. This cultivar is adapted to low maintenance conditions and has the ability to maintain growth and color later into the fall than other warm season grasses.

3 Drawing Sheets

BACKGROUND OF THE INVENTION

Buffalograss, *Buchloe dactyloides* (Nutt) Engelm., is a perennial, low growing, drought tolerant species native to the Central and Southern Great Plains that spreads by profusely branching stolons and thrives under semi-arid conditions with heavy to moderate grazing.

SUMMARY OF THE INVENTION

609 Buffalograss is distinguished from other commercially available cultivars in being a vegetatively propagated female plant with a darker green color than 'Prairie' Buffalograss. 609 Buffalograss has better overall quality, appearance, density and uniformity than seeded varieties. It has a vigorous, low growing growth habit and is more competitive than all commercially available Buffalograsses, other than Prairie. 609 Buffalograss provides an attractive, wear tolerant turf which requires less water, fertilizer and mowing than other turfgrass species. These characteristics, along with on-site testing, having shown that 609 Buffalograss is well adapted to golf course roughs, home lawns, and institutional areas requiring a reduced management level.

A single plant of the genotype 609 Buffalograss was selected from a nursery of plants. The nursery of plants from which the selection was made was grown from a single female plant designated TAES 1321.1. This nursery was not maintained after 1984, in Texas and the germ plasm was transferred to Nebraska. The single female plant TAES 1321.1 had been selected from a field grown from seed. The seed was from an open pollinated hybridization nursery of: (1) a plant found in a native stand in 1980 in Austin, Tex. designated TAES 1321; and, (2) 149 other native ascessions.

This female genotype was found in a plot labeled 1321.1 which was originally collected in Austin, Tex. This selection was identified as NE 84-609 and evaluated at the John Seaton Anderson Turfgrass Research Facility near Mead, Nebraska. The female genotype was propagated vegetatively by stolons and pre-rooted plugs to provide planting stock for studying performance and making comparisons to "Texoka", a commercial standard; "Prairie", a new release from Texas A&M.

BRIEF DESCRIPTION OF THE ILLUSTRATIONS

Figure 5:
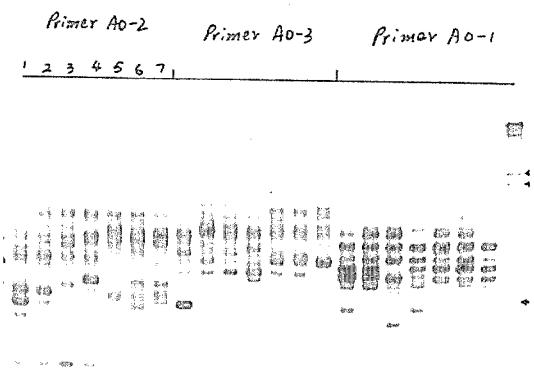

FIG. 5 is a photograph of PCR DNA Fingerprint for Buffalograsses: NE 84-609—No. 5; Prairie—No. 7; and NE 84-378—No. 6, University of California—Davis, Dr. Lin Wu.

Figure 6:
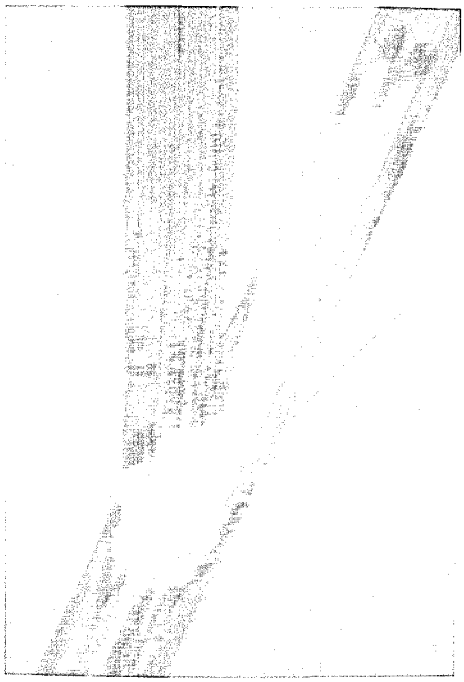

FIG. 6 is a photograph of a NE 84-609 plant.

DETAILED DESCRIPTION OF THE PLANT

The excellent overall turfgrass quality, rate of establishment, good cold tolerance, high density and drought tolerance of Buffalograss along with other information allow this genotype to be distinguished from other Buffalograsses. Vegetative propagation of 609 Buffalograss from plugs or sod pieces permits maintenance of cultivar with no genetic variation.

Gentotype Buffalograss is a female plant from a dioecious species which has a yellow anther color. The growth characteristics of buffalograss can be used to distinguish one cultivar from others. 609 Buffalograss, Prairie, Texoka and the Nebraska experimentals are all female clones, but eventually male clones will be developed.

The internodes of 609 Buffalograss are similar to "Texoka" in width, but longer in length (Table 1). The length of internode one of 609 Buffalograss is longer than NE 84-315 and NE 84-378, but internode widths are all the same. The tiller leaf blade width is similar to "Texoka" and other experimentals, but the tiller leaf blade length is much smaller for all tillers measured (Tables 2 and 3). Measurements of the spikelet and length indicate that Buffalograss has a shorter spikelet than the standard "Texoka" (Table 4). At the UNL research facility, 609 Buffalograss produced more, lower growing inflorescences than Texoka or NE 84-315. 609 Buffalograss had inflorescences comparable to NE 85-378; however, its canopy is medium and NE 85-378 is open (Table 5).

609 Buffalograss has been evaluated at several locations throughout the United States. In most tests 609 Buffalograss was compared to "Texoka" a commercial standard; "Prairie" a new release from Texas A&M; and other experimentals which are being considered for release.

609 Buffalograss had an excellent rate of establishment (Tables 6 and 7). The Texas A&M-Dallas trial shows that 609 Buffalograss and "Prairie", both well adapted to the deep South, had better establishment than "Texoka" or other Nebraska selections. The Southern Illinois study indicated that 609 Buffalograss showed slower establishment than the better adapted northern selections, and was more sensitive to over applications of Princip® (Table 8). Stolen production and stolon length at Texas A&M-Dallas showed that 609 Buffalograss produced more stolons and larger stolons than "Texoka" or other Nebraska selections (Table 9). At Nebraska, 609 Buffalograss exhibited excellent establishment in all plantings, including increases of material for plant breeders' nurseries and experimental plot area. David Doguet, of Crenshaw & Doguet Turfgrass, Inc., reported that 609 Buffalograss showed slightly faster establishment than "Prairie" buffalograss under sod farm conditions.

Figure 1:
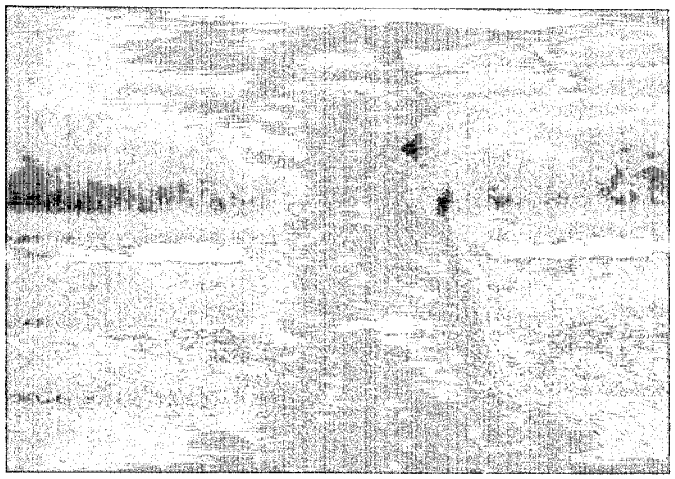
FIG. 1 is a photograph showing a field of NE 84-609 on the right and a field of Prairie Buffalograss on the left.
Figure 2:
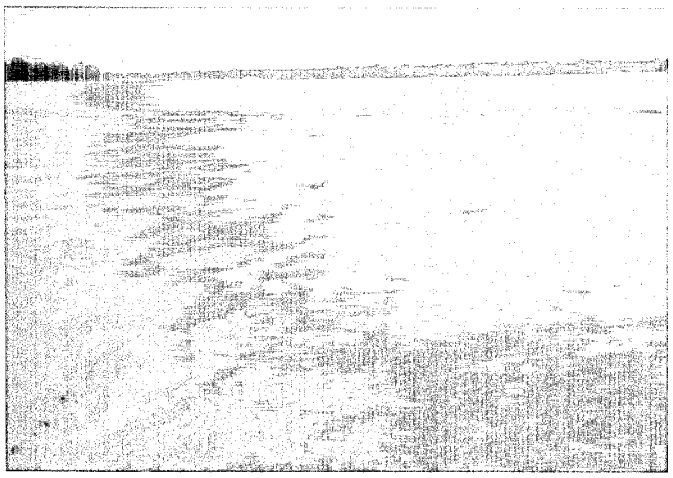
FIG. 2 is a photograph showing a field of NE 84-609 Buffalograss sod below and Prairie at the top.
Figure 3:
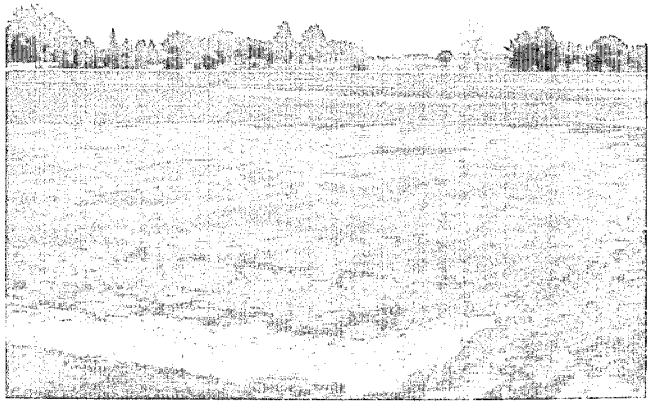
FIG. 3 is a photograph showing a NE 84-609 breeder's field.
Figure 4:
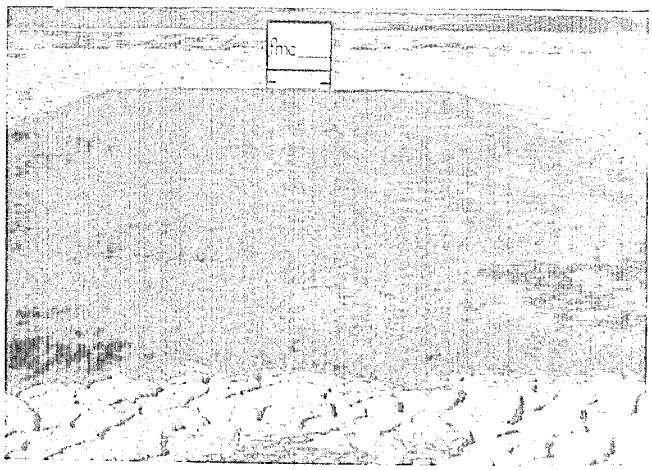
FIG. 4 is a photograph of NE 84-609 in Arizona.

The most definitive way to differentiate 609 from "Prairie" is a DNA fingerprint. Work conducted at the University of California-Davis has distinguished 609 Buffalograss from "Prairie" with at least two primers. Primer AO-1 provides a very clear separation of these two cultivars (FIG. 1).

Buffalograss is a warm season species and will green up later and go dormant earlier than cool season species such as Kentucky bluegrass. Although this characteristic may be a negative in the northern part of the United States, buffalograss may have a longer growing season than other warm season turfgrasses in the South. Spring green-up has been evaluated at both the University of Nebraska and at Texas A&M-Dallas. 609 Buffalograss had a spring green-up rate similar to Texoka in Nebraska and similar to Prairie in Texas (Tables 10 and 11). Although an earlier spring green-up and a later dormancy in the North would be advantageous, it is possible that cold hardiness would be lost. 609 Buffalograss may have slightly less cold hardiness than Texoka when grown in the North.

Turfgrass color is an important component of turfgrass quality. At Texas A&M-Dallas, 609 Buffalograss had color ratings superior to the commercial standards Texoka and Prairie. (Tables 12 and 13).

Turfgrass quality is a rating used to indicate the aesthetic value of a turf cultivar. This characteristic is very important in buffalograss because its turf characteristics have been overlooked in the past. 609 Buffalograss had outstanding turfgrass quality at each location in the South (Tables 14, 15, 16, and 17). In each location, 609 Buffalograss had quality comparable or superior to Prairie, Texoka and Nebraska experimentals. At the University of Nebraska, 609 Buffalograss had turfgrass quality ratings comparable to Texoka in the spring and higher ratings during the summer (Table 18). At the Crenshaw & Douget sod farm, Bastrop, Tex., 609 Buffalograss had an excellent, high quality sod.

Reduced water use and drought stress avoidance are important characteristics of drought resistance in buffalograss, contributing to its lower maintenance cost. 609 Buffalograss has been shown to have drought stress tolerance at University of Arizona (Table 19) and at the University of Nebraska (Table 22). Water use rates of 609 Buffalograss have been comparable to Texoka and Prairie in Nebraska (Table 23). The water use rates of all three cultivars are less than those of other turf species.

Density is an important component of turfgrass quality. In studies at the University of Arizona and at the University of Nebraska, 609 Buffalograss had turfgrass density ratings equal to or better than Texoka (Table 24). This density has permitted 609 Buffalograss sod to be harvested three months after planting at the Crenshaw & Douget sod farm.

The Variety

Origin: Cultivar of a single superior female plant selected from the progeny of a plant collected in Austin, Tex., and open-pollinated by a collection of native accessions from the Great Plains.

Classification:
- *Botanic.*—*Buchloe dactyloids* (Nutt.) Engelm.
- *Chromosome number.*—2n chromosomes=40.

Form: Monocot gramineae.

Growth habit: A perennial female plant, with a stoloniferous growth habit, which allows it to be vegetatively propagated. It is able to spread rapidly under non-competitive conditions when conditions are favorable for stolon production. It has a very fibrous root system which can have a depth of 100 to 150 cm. It will produce a dense, fine textured turf with excellent color throughout most of the growing season.

Establishment rate:
- *Plugs.*—8 to 10 weeks with irrigation.
- *Sod.*—1 to 2 weeks.
- *Sprigs.*—Not recommended.

Adaptation: North/South from the Nebraska-South Dakota border to Central Mexico and East/West from Georgia to California.

Blade:
- *Shape.*—Long, slender.
- *Length (mature).*—Approximately 10–12 cm.
- *Width.*—Approximately 1.0–1.1 mm.
- *Pubescence.*—Minimal compared to other buffalograsses.

Mature plant height: 10 to 12 cm.

Above canopy stolon production: minimal compared to Prairie.

Internode length: 4–10 cm (internode 1).

Internode width: 0.9 mm.

Node pigmentation: green.

Stolon color[1]:
- *Midsummer.*—Typically green (143B).
- *Late fall.*—Purple (65D) or green (142B).
- *Winter.*—Brown (164C).

Leaf Color:
- *Midsummer.*—Bluegreen (141C) to dark green (141A).
- *Winter.*—Brown (164C).

Soil adaptation:
- *Heavy soils.*—Silty clay loam preferred, slightly acid to alkaline pH.

Female inflorescence: Present, but not readily apparent.
Male inflorescence: Absent.
[1]RHA Colour Chart Designations

COMPARATIVE DATA

The following tables provide data comparisons of selected characteristics between 609 Buffalograss, Prairie, Texoka and Nebraska experimentals.

TABLE 1

Internode Length and Width:
University of Nebraska Greenhouse
Winter 1988

| | Internode Length (cm)[1] | | Internode Width (mm)[1] | |
|---|---|---|---|---|
| | Internode 1 | Internode 2 | Internode 1 | Internode 2 |
| 609 Buffalograss | 7.2 ± 3.0 | 2.0 ± 2.5 | 0.9 ± 0.1 | 0.9 ± 0.2 |
| Texoka | 6.6 ± 1.7 | 6.2 ± 0.4 | 0.8 ± 0.1 | 0.9 ± 0.1 |
| NE 84-315 | 4.2 ± 0.7 | 4.3 ± 0.9 | 0.8 ± 0.1 | 0.8 ± 0.1 |
| NE 85-378 | 4.7 ± 0.9 | 4.4 ± 0.4 | 0.8 ± 0.1 | 0.8 ± 0.1 |

[1]Average of 10 measurements

TABLE 2

Leaf Tiller Length Characteristics:
University of Nebraska Greenhouse
Winter 1988

| | Leaf Tiller Length[1] | | | |
|---|---|---|---|---|
| | Right Tiller | | Left Tiller | |
| | Tiller 1 | Tiller 2 | Tiller 1 | Tiller 2 |
| 609 Buffalograss | 3.5 ± 1.0 | 1.9 ± 0.9 | 2.8 ± 1.0 | 1.8 ± 0.5 |
| Texoka | 4.8 ± 1.8 | 3.9 ± 1.5 | 5.6 ± 2.3 | 4.5 ± 1.6 |
| NE 84-315 | 4.0 ± 1.2 | 3.1 ± 1.2 | 3.7 ± 1.6 | 2.9 ± 1.2 |
| NE 85-378 | 5.1 ± 1.8 | 2.9 ± 1.3 | 4.5 ± 1.1 | 3.2 ± 1.7 |

[1]Average of 10 measurements

TABLE 3

Leaf Tiller Width Characteristics:
University of Nebraska Greenhouse
Winter 1988

| | Leaf Tiller Width (mm)[1] | | | |
|---|---|---|---|---|
| | Right Tiller | | Left Tiller | |
| | Tiller 1 | Tiller 2 | Tiller 1 | Tiller 2 |
| 609 Buffalograss | 1.2 ± 0.1 | 1.1 ± 0.5 | — | — |
| Texoka | 1.2 ± 0.2 | 1.3 ± 0.4 | 1.2 ± 0.2 | 1.3 ± 0.4 |
| NE 84-315 | 1.2 ± 0.2 | 1.3 ± 0.3 | 1.2 ± 0.2 | 1.2 ± 0.3 |
| NE 85-378 | 1.2 ± 0.2 | 1.4 ± 0.1 | 1.1 ± 0.2 | 1.3 ± 0.1 |

[1]Average of 10 measurements

TABLE 4

Spikelet Length Characteristics:
University of Nebraska John Seaton Anderson
Turfgrass Research Facility
Summer 1991

| | Spikelet Length (cm)[1] |
|---|---|
| 609 Buffalograss | 3.5 ± 0.7 |
| Texoka | 10.8 ± 2.0 |
| NE 84-315 | 3.9 ± 1.0 |
| NE 85-378 | 4.2 ± 1.1 |

[1]Average of 20 measurements

TABLE 5

Canopy Density and Inflorescence Characteristics:
JSA Buffalograss Trial, 7/4/89
(Established June 1987)

| Experimental | Canopy Density[1] | Inflorescense | Inflorescense Height (cm) |
|---|---|---|---|
| 609 Buffalograss | 2.2 a* | 21.2 abc | 2.8 c |
| Texoka | 2.2 a | 10.5 b c | 8.9 b |
| NE 84-315 | 1.2 b | 7.0 c | 13.4 a |

TABLE 5-continued

Canopy Density and Inflorescence Characteristics:
JSA Buffalograss Trial, 7/4/89
(Established June 1987)

| Experimental | Canopy Density[1] | Inflorescense | Inflorescense Height (cm) |
|---|---|---|---|
| NE 84-378 | 1.2 b | 17.8 abc | 2.4 c |

[1]Canopy Density is rated 1 = open, 2 = average, 3 = closed
*Means within a column followed by the small letter and not significantly different using the Waller-Duncan multiple comparison procedures (K = 100)

TABLE 6

Establishment Vigor:
1990 Colorado State Buffalograss Trial
Fort Collins, Colorado[1] (Est. 9/89)

| | Establishment Vigor[2] | | |
|---|---|---|---|
| Experimental | May | July | % 6/13 Spring Survival |
| 609 Buffalograss | 2.7[1] | 3.3 | 92 |
| Prairie | 1.7 | 1.7 | 33 |
| Texoka | 3.0 | 3.7 | 100 |
| NE 84-315 | 2.3 | 3.0 | 100 |
| NE 85-378 | 3.0 | 4.0 | 100 |
| LSD (.05) | 0.9 | — | — |

[1]Data taken by Dr. R. Cuany
[2]1 to 4 scale with 4 best establishment vigor
LSD (.05)

TABLE 7

Percent Cover:
Buffalograss Regional Trial, Dallas TX[1]
(Est. 5/17/88)

| Experimental | 6/23/88 | 7/26/88 | 3/25/89 | 4/8/89 |
|---|---|---|---|---|
| 609 Buffalograss | 19.3 ab* | 41.3 ab | 87.7 a | 88.3 a |
| Prairie | 21.0 a | 56.7 a | 96.7 a | 100.0 a |
| Texoka | 12.3 bc | 21.0 c | 78.3 ab | 85.0 ab |
| NE 84-315 | 7.3 c | - 18.0 c | 60.0 b | 70.0 b |
| NE 85-378 | 7.3 c | 19.3 c | 80.0 a | 86.7 ab |

*Means within a column followed by the small letter and not significantly different using the Waller-Duncan multiple comparison procedures (K = 100)
[1]Data taken by Dr. B. Ruemmele

TABLE 8

Establishment Percent Cover 1990:
Southern Illinois Buffalograss Trial
Carbondale, Illinois[1] (Est. 5/34/90)

| | Establishment Percent Cover | | | | |
|---|---|---|---|---|---|
| Experimental | 6/12 | 7/17 | 8/15[2] | 9/17 | 10/18 |
| 609 Buffalograss | 25.0 a* | 53.3 d | 5.0 b | 33.3 b | 55.0 b |
| Texoka | 20.7 a | 83.3 abc | 63.3 a | 86.7 a | 91.7 a |
| NE 84-315 | 25.0 a | 98.3 a | 83.3 a | 98.7 a | 99.7 a |
| NE 85-378 | 17.3 a | 90.0 ab | 78.3 a | 96.0 a | 96.7 a |

*Means within a column followed by the small letter and not significantly different using the Waller-Duncan multiple comparison procedures (K = 100)
[1]Data taken by Dr. K. Diesburg
[2]Herbicide Damage Occurred
LSD (.05)

TABLE 9

Stolon Production and Length 1988:
Buffalograss Regional Trial, Dallas, TX[1]
(Est. 5/17/88)

| | # Stolons | Stolon Length cm. | | |
|---|---|---|---|---|
| Experimental | 49 days | 49 days | 57 days | 70 days |
| 609 Buffalograss | 10.7 ab* | 6.1 a | 8.0 a | 10.6 a |
| Prairie | 17.1 a | 5.4 ab | 7.5 ab | 9.5 ab |
| Texoka | 4.1 b | 2.5 c | 4.9 cde | 6.5 d |
| NE 84-315 | 8.1 b | 2.6 c | 3.5 e | 5.1 d |

TABLE 9-continued

Stolon Production and Length 1988:
Buffalograss Regional Trial, Dallas, TX[1]
(Est. 5/17/88)

| Experimental | # Stolons 49 days | Stolon Length cm. 49 days | 57 days | 70 days |
|---|---|---|---|---|
| NE 84-378 | 4.0 b | 2.2 c | 4.4 de | 6.1 d |

*Means within a column followed by the small letter and not significantly different using the Waller-Duncan multiple comparison procedures (K = 100)
[1]Data taken by Dr. B. Ruemmele

TABLE 10

Spring Greenup:
JSA Buffalograss Trial, Mead, Nebraska 1989
(Est. June 1987)

| Experimental | Spring Greenup 4/25 | 5/4 | 5/11 |
|---|---|---|---|
| 609 Buffalograss | 3.5 a* | 6.6 a | 7.0 a |
| Texoka | 3.5 a | 7.0 a | 7.6 a |
| NE 84-315 | 1.8 b | 4.8 b | 5.5 b |
| NE 85-378 | 1.8 b | 4.4 b | 5.5 b |

Spring greenup is rated 1-9, with 9 = most green
*Means within a column followed by the small letter and not significantly different using the Waller-Duncan multiple comparison procedures (K = 100)

TABLE 11

Percent Spring Greenup:
Buffalograss Regional Trial, Dallas, Texas[1]
(Est. 5/17/88)

| Experimental | Percent Spring Greenup 3/15/89 | 3/22/89 | 3/29/89 | 4/5/89 | 4/15/89 |
|---|---|---|---|---|---|
| 609 Buffalograss | 20.0 c* | 40.0 a | 83.3 b | 96.3 ab | 99.0 |
| Prairie | 40.0 b | 40.0 b | 73.3 b | 93.3 b | 99.0 |
| Texoka | 20.0 c | 50.0 ab | 95.0 a | 97.7 a | 99.0 |
| NE 84-315 | 8.0 c | 43.3 b | 98.3 a | 99.0 a | 99.0 |
| NE 85-378 | 18.0 c | 50.0 ab | 91.7 a | 97.7 a | 99.0 |

*Means within a column followed by the small letter and not significantly different using the Waller-Duncan multiple comparison procedures (K = 100)
[1]Data taken by B. Ruemmele

TABLE 12

Turfgrass Color 1989-90
Buffalograss Regional Trial
Dallas, Texas (Est. 5/17/88)

| Entry | Turfgrass Color[2] 1989 20 Jun | 10 Aug | 13 Sep | 21 Sep | 31 Oct | 23 Nov | 1990 04 Jan | 24 Jan |
|---|---|---|---|---|---|---|---|---|
| 609 Buffalograss | 6.7 | 7.0 | 7.0 | 7.3 | 7.3 | 7.0 | 2.3 | 1.0 |
| Prairie | 5.0 | 3.7 | 4.3 | 3.3 | 4.3 | 5.0 | 2.3 | 1.0 |
| Texoka | 6.7 | 4.3 | 1.3 | 1.3 | 1.7 | 1.3 | 1.7 | 1.0 |
| NE 84-315 | 7.3 | 8.7 | 1.7 | 2.7 | 1.3 | 1.0 | 1.0 | 1.0 |
| NE 85-378 | 6/7 | 7/7 | 1.3 | 2.0 | 1.0 | 1.0 | 1.0 | 1.0 |
| C.V. | 21.5 | 16.0 | 25.9 | 31.7 | 24.8 | 30.2 | 22.3 | 0.0 |

[1]Data taken by Dr. B. Ruemmele
[2]Turfgrass color is rated 1-9, with 1 = brown, 5 = med green, and 9 = dark green

TABLE 13

Turfgrass Color:
1990 Season Buffalograss Clonal Evaluation
John Seaton Anderson Facility
Mead, Nebraska (Est. 1986)

| Experimental | Turfgrass Color[1] 6/8 | 6/15 | 7/30 | 8/10 | 9/13 | AVG |
|---|---|---|---|---|---|---|
| 609 Buffalograss | 6.0 | 5.8 | 7.3 | 6.8 | 7.3 | 6.6 |
| Texoka | 5.5 | 5.8 | 6.8 | 6.3 | 7.0 | 6.3 |
| NE 84-315 | 8.0 | 7.3 | 6.8 | 6.3 | 7.3 | 7.1 |
| NE 85-378 | 7.8 | 7.0 | 5.3 | 7.3 | 7.1 | 6.9 |

TABLE 13-continued

Turfgrass Color:
1990 Season Buffalograss Clonal Evaluation
John Seaton Anderson Facility
Mead, Nebraska (Est. 1986)

| Experimental | Turfgrass Color[1] 6/8 | 6/15 | 7/30 | 8/10 | 9/13 | AVG |
|---|---|---|---|---|---|---|
| MEANS | 6.8 | 6.5 | 6.6 | 6.7 | 7.2 | 6.7 |
| LSD (0.05) | 1.2 | 1.4 | 1.1 | 1.2 | 1.1 | — |

[1]Turfgrass color is rated 1-9, with 1 = brown, 5 = med green, and 9 = dark green.

TABLE 14

Turfgrass Quality:
1990 University of Arizona Buffalograss Trial[1]
(Est. 9/4/88)

| Experimental | Turfgrass Quality[2] 5/9 | 5/29 | 6/13 | 6/24 | 7/29 |
|---|---|---|---|---|---|
| 609 Buffalograss | 5.3 a* | 6.9 a | 8.3 a | 8.0 a | 7.0 a |
| Prairie | 3.7 ab | 6.8 a | 8.0 a | 8.0 a | 7.0 a |
| Texoka | 5.0 a | 4.3 b | 5.3 b | 5.3 b | 3.7 bc |
| NE 84-315 | 5.3 a | 6.8 a | 7.3 a | 7.3 a | 3.3 c |
| NE 85-378 | 5.0 a | 6.6 a | 8.0 a | 8.0 a | 4.3 b |

| Experimental | Turfgrass Quality[2] 9.6 | 10/31 | 11/15 | 11/25 | 12/20 |
|---|---|---|---|---|---|
| 609 Buffalograss | 5.7 a | 5.3 a | 5.7 a | 4.7 a | 4.7 a |
| Prairie | 4.0 abc | 4.0 b | 5.3 a | 4.3 a | 3.0 bc |
| Texoka | 3.7 bcd | 1.7 c | 2.3 b | 2.0 b | 2.0 cd |
| NE 84-315 | 2.0 d | 2.0 c | 1.7 bc | 2.0 b | 2.0 cd |
| NE 85-378 | 2.7 cd | 2.0 c | 2.3 b | 2.0 b | 2.0 cd |

[1]Turfgrass color is rated 1-9, with 1 = brown, 5 = med green, and 9 = dark green

TABLE 15

Turfgrass Quality:
Buffalograss Regional Trial, Dallas Texas[1]
(Est. 5/17/88)

| Entry | Turfgrass Quality[2] 08 Apr | 06 May | 27 May | 20 Jun | 10 Aug | 13 Sep | 21 Sep |
|---|---|---|---|---|---|---|---|
| 609 Buffalograss | 6.3[2] | 7.3 | 8.0 | 7.3 | 9.0 | 7.7 | 8.7 |
| Prairie | 6.0 | 7.3 | 7.0 | 8.0 | 7.7 | 7.3 | 7.7 |
| Texoka | 4.7 | 6.0 | 6.3 | 6.0 | 6.3 | 4.0 | 4.7 |
| NE 84-315 | 6.0 | 7.3 | 6.0 | 5.7 | 6.3 | 3.3 | 3.7 |
| NE 84-378 | 5.3 | 7.7 | 7.3 | 7.0 | 7.0 | 4.0 | 4.7 |
| MSD[3] | 2.4 | n.s.[4] | 1.6 | 1.5 | 1.8 | 0.9 | 1.0 |

| Entry | Turfgrass Quality[2] 31 Oct | 23 Nov | 04 Jan | 24 Jan | 25 Feb | 12 Date Avg |
|---|---|---|---|---|---|---|
| 609 Buffalograss | 9.0 | 8.7 | 7.0 | 6.0 | 5.7 | 7.6 |
| Prairie | 8.3 | 8.3 | 7.0 | 6.0 | 5.7 | 7.2 |
| Texoka | 4.0 | 4.7 | 4.3 | 4.0 | 3.7 | 4.9 |
| NE 84-315 | 3.3 | 3.3 | 3.3 | 3.0 | 3.0 | 4.5 |
| NE 84-378 | 5.0 | 4.3 | 4.3 | 4.3 | 3.3 | 5.4 |
| MSD[3] | 1.7 | 1.3 | 1.0 | 0.5 | 1.0 | 0.5 |

[1]Data taken by Dr. B. Ruemmele
[2]Turf quality is rated 1-9, 9 = best
[3]MSD = Minimum significant Difference to separate classes within each column using the Waller Duncan K ratio T Test (K ratio = 100)
[4]n.s. indicates dates where no significant differences were determined among the means

TABLE 16

Turfgrass Quality Buffalograss Regional Trial[1], 1990, Dallas, Texas
(Est. 5/17/88)

| | Turfgrass Quality[2] May 9 | May 29 | June 24 | July 29 | Sep 24 |
|---|---|---|---|---|---|
| 609 | 5.3 a[3] | 8.3 a | 8.0 a | 7.0 a | 5.7 a |

TABLE 16-continued

Turfgrass Quality Buffalograss Regional Trial[1], 1990, Dallas, Texas (Est. 5/17/88)

| | | | | | |
|---|---|---|---|---|---|
| Buffalograss | | | | | |
| Prairie | 3.7 ab | 8.0 a | 8.0 a | 7.0 a | 4.0 abc |
| Texoka | 5.0 a | 5.3 b | 5.0 b | 3.7 bc | 3.7 bcd |
| NE 84-315 | 5.3 a | 7.3 a | 5.7 b | 3.3 c | 2.0 d |
| NE 85-378 | 5.0 a | 8.0 a | 5.3 b | 4.3 b | 2.7 cd |

| | Turfgrass Quality[2] | | | | |
|---|---|---|---|---|---|
| | Oct 31 | Nov 15 | Nov 25 | Dec 20 | Dec 20 |
| 609 | 5.3 a | 5.7 a | 4.7 a | 4.7 a | 5.7 a |
| Buffalograss | | | | | |
| Prairie | 4.0 b | 5.3 a | 4.3 a | 3.0 bc | 5.0 ab |
| Texoka | 1.7 c | 2.3 b | 2.0 b | 2.0 cd | 3.3 c |
| NE 84-315 | 2.0 c | 1.7 bc | 2.0 b | 2.0 cd | 3.0 c |
| NE 85-378 | 2.0 c | 2.3 b | 2.0 b | 2.0 cd | 3.0 c |

[1]Data taken by Dr. B. Ruemmele

[2]Turfgrass quality is sum of color and density. For Dec 20 dates, first quality includes density for green tissue and second quality includes density of all tissue (ground coverage). Density 1-9, 9 = densest - for green tissue only except second Dec 20 date which is density of all tissue regardless of color.

[3]Means within a column followed by the small letter are not significantly different using the Waller-Duncan multiple comparison procedures (K = 100)

TABLE 17

Turfgrass Quality 1990: University of Georgia, Tipton, GA[1]

| | Turfgrass Quality[2] | | | |
|---|---|---|---|---|
| Experimental | 6/14 | 7/7 | 9/15 | 10/24 |
| 609 Buffalograss | — | 2.0 | 6.0 | 6.0 |
| Prairie | 3.0 | 2.0 | 6.5 | 6.5 |
| Texoka | 2.0 | 4.5 | 5.5 | 4.5 |
| NE 84-315 | — | 3.5 | 6.5 | 7.0 |
| NE 85-378 | — | 3.5 | 6.5 | 6.0 |
| LSD (.05) | .8 | 1.1 | 1.8 | 1.5 |

[1]Data taken by Dr. W. Hanna

[2]Turfgrass Quality: 1-9, 9 = best

TABLE 18

Turfgrass Quality: 1990 Season Buffalograss Clonal Evaluation John Seaton Anderson Facility, Mead, Nebraska (Est. 1986)

| | Turfgrass Quality[1] | | | | | |
|---|---|---|---|---|---|---|
| Experimental | 6/8 | 6/15 | 7/30 | 8/10 | 9/13 | AVG |
| 609 Buffalograss | 3.3 | 3.0 | 5.0 | 6.5 | 7.0 | 5.0 |
| Texoka | 3.8 | 3.8 | 4.3 | 5.3 | 5.0 | 4.4 |
| NE 84-315 | 6.3 | 6.5 | 5.3 | 4.8 | 5.5 | 5.7 |
| NE 85-378 | 7.3 | 5.8 | 5.8 | 5.5 | 4.8 | 5.8 |
| LSD (0.05) | 1.3 | 1.5 | 1.3 | 1.4 | 2.4 | — |

[1]Turfgrass Quality is rated 1-9, 9 = best

TABLE 19

Summer Stress: 1990 University of Arizona Buffalograss Trial[1] (Est. 9/4/89)

| | Summer Stress[2] June 24-July 29, 1990 | | | |
|---|---|---|---|---|
| Experimental | Stress 1 | Stress 2 | Stress 3 | Stress 4 |
| 609 Buffalograss | 8.0 a[3] | 8.0 a | 7.0 a | 6.7 a |
| Prairie | 8.0 a | 8.0 a | 7.3 a | 6.3 a |
| Texoka | 6.3 b | 6.7 b | 5.3 b | 5.0 b |
| NE 84-315 | 6.3 b | 5.7 c | 4.0 c | 3.0 c |
| NE 85-378 | 6.3 b | 4.7 d | 3.7 c | 2.3 c |

[1]Data taken by Dr. C. Mancino

[2]Summer Stress is rated 9 to 1 with 9 = no stress and 1 dormant

[3]Means within a column followed by the small letter and not significantly different using the Waller-Duncan multiple comparison procedures (K = 100)

TABLE 20

Comparative Dehydration Avoidance, as Accessed by Percent Fixing, of Buffalograss Observed During 48 Days of Drought Stress During the Summer of 1989 College Station, Texas[1] Dehydration Avoidance

| Experimental | Dehydration Avoidance Rating[2] |
|---|---|
| 609 Buffalograss | Very High |
| Prairie | Low |
| NE 84-315 | Very High |
| NE 85-378 | Very High |

[1]Data taken by Dr. J. Beard

[2]Dehydration Avoidance Rating: Very High, High, Medium, Low

TABLE 21

Comparative Drought Resistance evaluated as shoot recovery of buffalograss observed 30 days following rewetting, after 48 days of drought stress in 1989, College Station, Texas[1] Comparative Drought Resistance

| Experimental | Comparative Drought Resistance[2] |
|---|---|
| 609 Buffalograss | High[2] |
| Prairie | Low |
| NE 84-315 | High |
| NE 85-378 | High |

[1]Data taken by Dr. J. Beard

[2]Comparative Drought Resistance: High, Medium, Low

TABLE 22

Turfgrass Stress and Dormancy: 1990 Late Season Buffalograss Clonal Evaluation John Seaton Anderson, Mead, Nebraska (Established 1986)

| Experimental | Stress rating[1] 9/13 | Stress rating 10/2 | Dormancy rating[2] 10/2 |
|---|---|---|---|
| 609 Buffalograss | 2.5 | 3.8 | 2.7 |
| Texoka | 3.5 | 5.5 | 3.8 |
| NE 84-315 | 4.8 | 8.3 | 7.8 |
| NE 85-378 | 6.0 | 8.0 | 7.5 |
| Means | 4.2 | 6.4 | 5.5 |
| LSD (0.05) | 1.7 | 1.3 | 2.0 |

[1]Stress is rated 1 to 9, 9 = plot desiccation, 5 = partial plot desiccation, 1 = no plot desiccation (desiccation rated as amount of leaf firing and pale-green to brown spots forming on turf canopy).

[2]Dormancy is rated 1 to 9, 9 = completely dormant turfgrass with no green color or signs of plant growth, 5 = partially dormant turfgrass, 1 = non-dormant turfgrass.

TABLE 23

Water Use Rates 1990 John Seaton Anderson Buffalograss Research Trial

| | Water Use Rates[1] | | | |
|---|---|---|---|---|
| Experimental | 7/3-5 | 7/16-18 | 8/7-9 | 8/28-30 |
| 609 Buffalograss | 401.6 | 342.4 | 265.6 | 330.2 |
| Prairie | 454.5 | 359.1 | 269.0 | 323.8 |
| Texoka | 434.2 | 375.3 | 281.3 | 337.5 |
| LSD (0.05) | 56.1 | 43.1 | 17.3 | 92.8 |

[1]Water use rate is a three day total water use measured by grams water lost through evapotranspiration.

TABLE 24

Turfgrass Density: 1990 Season Buffalograss Clonal Evaluation John Seaton Anderson, Mead, Nebraska (Established 1986)

| | Turfgrass Density[1] | | | | | |
|---|---|---|---|---|---|---|
| Experimental | 6/8 | 6/15 | 7/30 | 8/10 | 9/13 | AVG |
| 609 Buffalograss | 2.5 | 3.8 | 4.3 | 6.3 | 6.8 | 4.7 |
| Texoka | 3.0 | 3.0 | 3.5 | 4.8 | 4.8 | 3.8 |
| 84-315 | 5.8 | 7.3 | 5.8 | 5.3 | 4.8 | 5.8 |
| 85-378 | 6.8 | 6.0 | 5.8 | 6.5 | 6.0 | 6.2 |
| MEANS | 6.8 | 6.5 | 6.6 | 6.7 | 7.2 | 6.7 |
| LSD (0.05) | 1.3 | 1.9 | 1.2 | 1.2 | 1.7 | — |

[1]Turfgrass Density is rated 1-9, 9 = most dense

What is claimed is:

1. A new and distinct perennial, female buffalograss cultivar as herein shown and described, distinguished by the characteristics described above.

* * * * *